US007624519B1

(12) United States Patent
Thorne

(10) Patent No.: US 7,624,519 B1
(45) Date of Patent: Dec. 1, 2009

(54) FOOT AND ANKLE PROTECTIVE APPARATUS

(76) Inventor: Robert G. Thorne, 803 N. 2nd St., Dennison, OH (US) 44621

( * ) Notice: Subject to any disclaimer, the term of this patent is extended or adjusted under 35 U.S.C. 154(b) by 338 days.

(21) Appl. No.: 11/695,540

(22) Filed: Apr. 2, 2007

(51) Int. Cl.
*A61F 5/00* (2006.01)
(52) U.S. Cl. ............... 36/110; 36/72 R; 602/27; 602/23
(58) Field of Classification Search ............ 36/110, 36/72 R; 602/23, 27, 3
See application file for complete search history.

(56) References Cited

U.S. PATENT DOCUMENTS

| 4,178,924 | A | | 12/1979 | Baxter |
| 4,378,793 | A | | 4/1983 | Mauldin et al. |
| 4,771,768 | A | * | 9/1988 | Crispin ............... 602/27 |
| D309,019 | S | | 7/1990 | Holden |
| 5,368,551 | A | * | 11/1994 | Zuckerman ............... 602/23 |
| 5,429,588 | A | * | 7/1995 | Young et al. ............... 36/28 |
| 6,021,780 | A | * | 2/2000 | Darby ............... 602/27 |

* cited by examiner

*Primary Examiner*—Ted Kavanaugh
(74) *Attorney, Agent, or Firm*—Crossley Patent Law; Mark A. Crossley

(57) ABSTRACT

A foot and ankle protective apparatus provides support and protection with simultaneous pliability. The apparatus is especially helpful to those who have recently had a cast removed and still require protection of the applicable area while allowing for walking. The apparatus comprises a thick, durable sole. Pliable leg, ankle and foot support is provided. The foot cover shell covers a stadium plate shaped cushion with a convex outer for fit to the identical shape of the shell. The concave inner of the cushion provides for comfortable fit to the top of the foot. The ankle opening between the foot surrounds and the leg surround overlaps allows for limited dorsi flexion and plantar flexion of the ankle, while still providing ankle support both laterally and against extreme flexion. The apparatus is especially useful in lieu of total immobilization.

1 Claim, 5 Drawing Sheets

FOOT AND ANKLE PROTECTIVE APPARATUS

BACKGROUND OF THE INVENTION

Foot and/or ankle immobilization after injury or surgery is common. Plaster casts are often used, as are other forms of casts, traction, and immobilization. Other immobilization devices have been developed which are an improvement over casts by virtue of their being removable and replaceable. What is lacking in the art is a device for use when a cast is not practical or indicated. Such a device is needed for those who have recently discarded a cast, for example, but are still in need of protection, stability, and at least partial immobility. Further, such a device is often needed when a full immobilization is not called for, even initially. Additionally, a device is needed which is adjustable with regard to stabilizing the foot or ankle, whereby a user dictates how snugly the device should fit. Such an adjustable fitting device can allow for swelling and reduced swelling, for example, which a cast cannot.

Additionally, such a device should provide protection over toes and the top of the foot, a trait sorely needed with users typically in sock feet or without even socks. The present apparatus provides quick ingress and egress of a user's foot and ankle. The present apparatus provides adjustable fit, so that a unique and therefore more expensive specifically fitted device need not be purchased. Further, the present apparatus provides for walking by allowing limited ankle flexion.

FIELD OF THE INVENTION

The foot and ankle protective apparatus relates to devices for immobilizing and supporting feet and ankles and more especially to an apparatus which supports and protects a foot and ankle while providing for walking.

DESCRIPTION OF THE PRIOR ART

Prior related art does not provide for the advantages of the present apparatus, such as limited ankle flexion, adjustability, and combined foot protection, all in waterproof materials. For example, U.S. Pat. No. 4,178,924 issued to Baxter on 1979 Dec. 18 teaches a cast protector for a typical rigid cast. U.S. Pat. No. 4,378,793 issued to Mauldin et al. on 1983 Apr. 5 teaches a removable ankle brace. The brace is entirely rigid, with buckles which are relatively inconvenient, and therefore cannot provide the walking capabilities of the present apparatus. U.S. Des. Pat. No. 309,019 issued to Holden on 1990 Aug. 3 teaches a rigid leg cast cover.

While the above-described devices fulfill their respective and particular objects and requirements, they do not describe a foot and ankle protective apparatus that provides for the advantages of the present foot and ankle protective apparatus. In this respect, the present foot and ankle protective apparatus substantially departs from the conventional concepts and designs of the prior art. Therefore, a need exists for an improved foot and ankle protective apparatus.

SUMMARY OF THE INVENTION

The general purpose of the foot and ankle protective apparatus, described subsequently in greater detail, is to provide a foot and ankle protective apparatus which has many novel features that result in an improved foot and ankle protective apparatus which is not anticipated, rendered obvious, suggested, or even implied by prior art, either alone or in combination thereof.

To attain this, the foot and ankle protective apparatus is made of pliable synthetic plastics, applicable polymers, rubbers, and the like which provide support and protection with simultaneous pliability. The cost effective apparatus protects a foot, ankle and lower leg of a person who is recovering from related problems. Such problems typically exist after injury, surgery, and the like. The apparatus is especially helpful to those who have recently had a cast removed and still require protection of the applicable area while providing for walking. The apparatus is also useful to those who have a stable lower extremity injury. The apparatus provides protected mobility to such persons.

The apparatus comprises a thick, durable sole. Pliable leg, ankle and foot support is provided. Padding is provided for the foot protective cover. The foot cover shell covers a stadium plate shaped cushion with a convex outer for fit to the identical shape of the shell. The concave inner of the cushion provides for comfortable fit to the top of the foot. The cushion lip extends beyond the shell so that the shell does not aggravate any part of the foot. The ankle opening between the foot surrounds and the leg surround overlaps allows for limited dorsi flexion and plantar flexion of the ankle, while still providing ankle support both laterally and against extreme flexion. The sides of the heel wrap lateral ankle support. The apparatus is especially useful in lieu of total immobilization, as with a cast, while providing needed support to an extremity that is in need of such.

Thus has been broadly outlined the more important features of the improved foot and ankle protective apparatus so that the detailed description thereof that follows may be better understood and in order that the present contribution to the art may be better appreciated.

An object of the foot and ankle protective apparatus is to stabilize a foot and ankle.

Another object of the foot and ankle protective apparatus is to adjustably fit a foot and ankle.

A further object of the foot and ankle protective apparatus is to provide protection for a foot.

An added object of the foot and ankle protective apparatus is to provide for walking.

And, an object of the foot and ankle protective apparatus is to provide foot cushioning.

Still another object of the foot and ankle protective apparatus is to provide for limited ankle flexion.

These together with additional objects, features and advantages of the improved foot and ankle protective apparatus will be readily apparent to those of ordinary skill in the art upon reading the following detailed description of presently preferred, but nonetheless illustrative, embodiments of the improved foot and ankle protective apparatus when taken in conjunction with the accompanying drawings.

In this respect, before explaining the current embodiments of the improved foot and ankle protective apparatus in detail, it is to be understood that the foot and ankle protective apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved foot and ankle protective apparatus. It is therefore important that the claims be regarded as including such equivalent constructions insofar as they do not depart from the spirit and scope of the foot and ankle protective apparatus.

It is also to be understood that the phraseology and terminology employed herein are for purposes of description and should not be regarded as limiting.

DETAILED DESCRIPTION OF THE DRAWINGS

Figure 1:
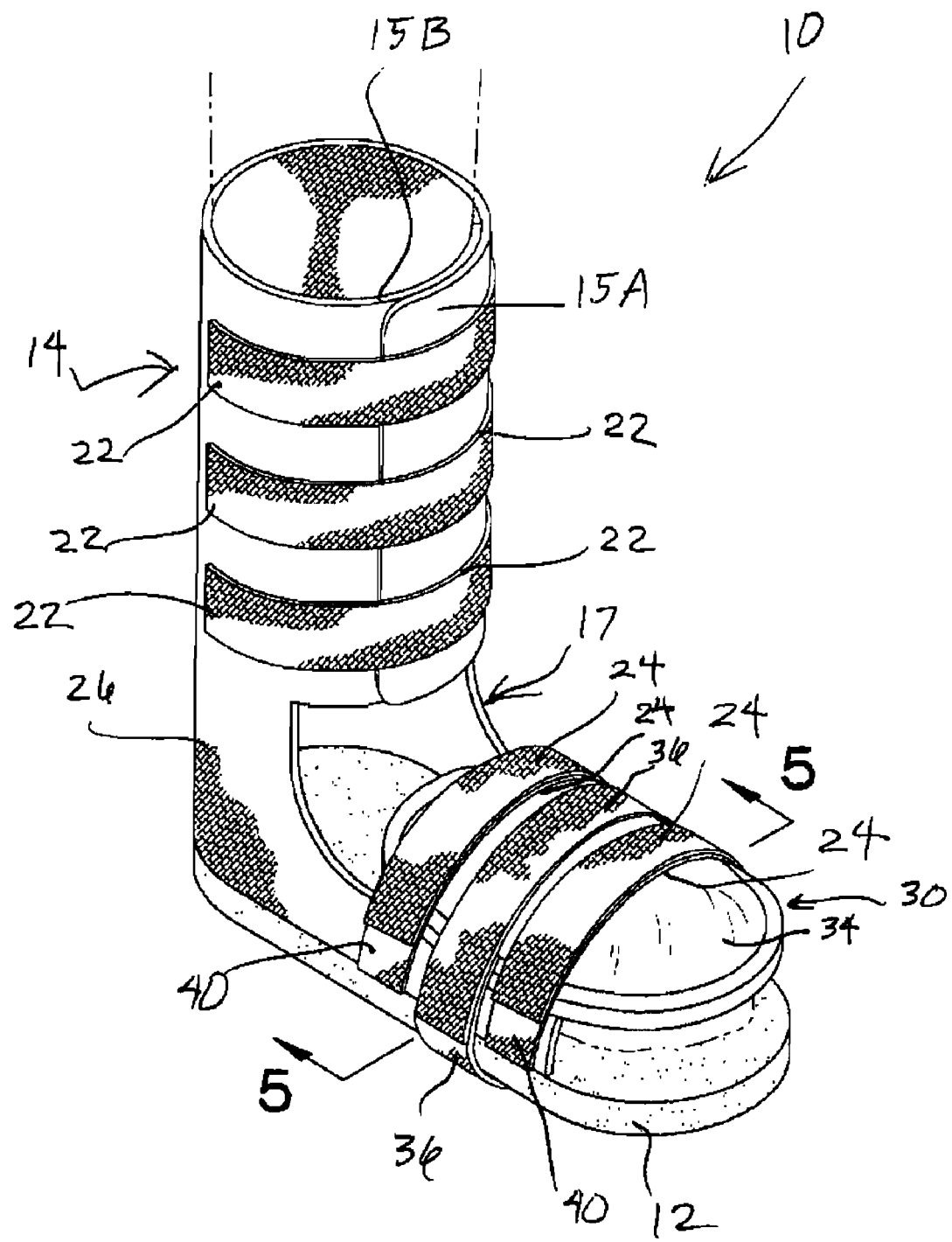
FIG. 1 is a perspective view.
Figure 2:
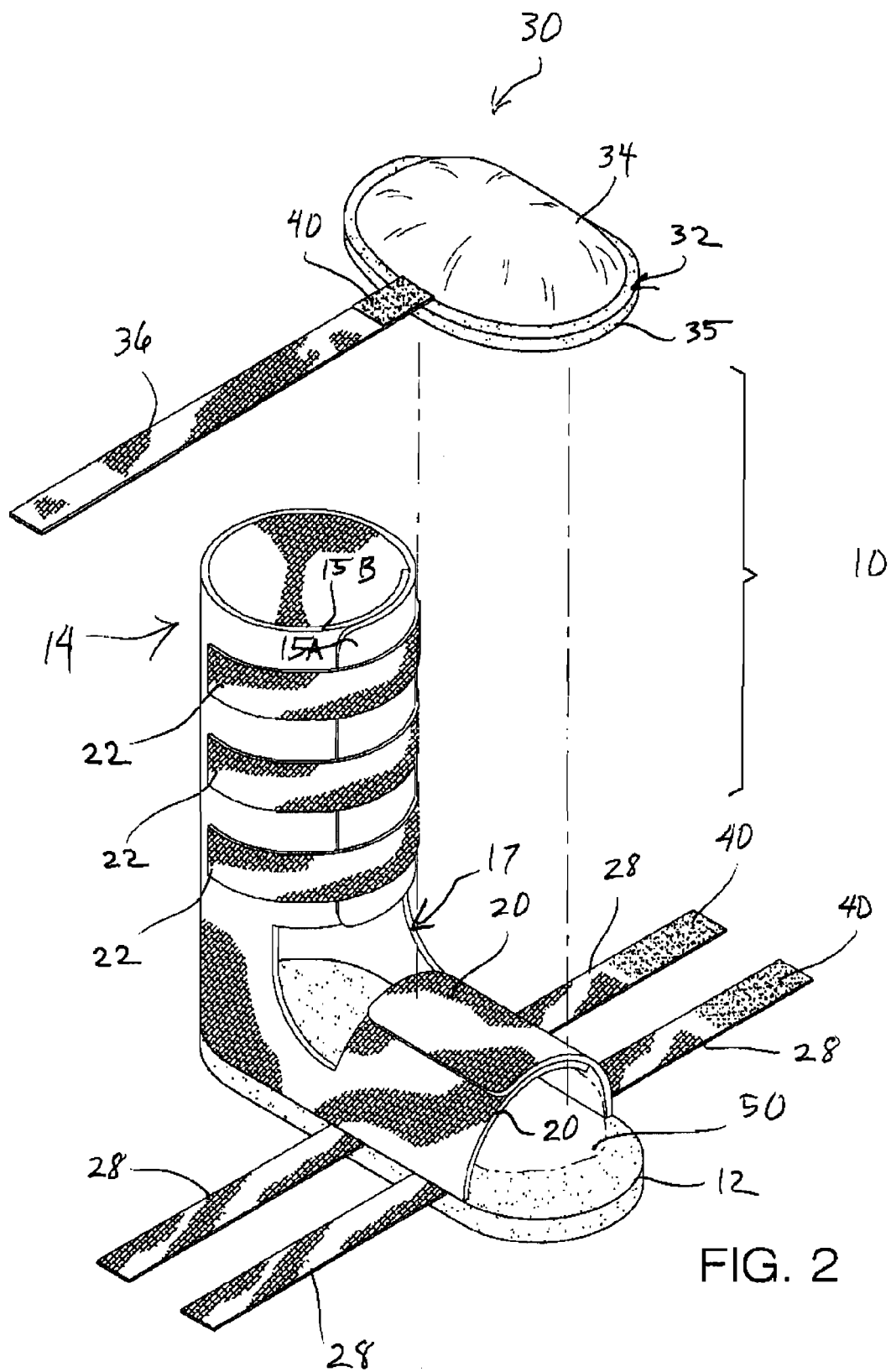
FIG. 2 is a partial exploded perspective view.
Figure 3:
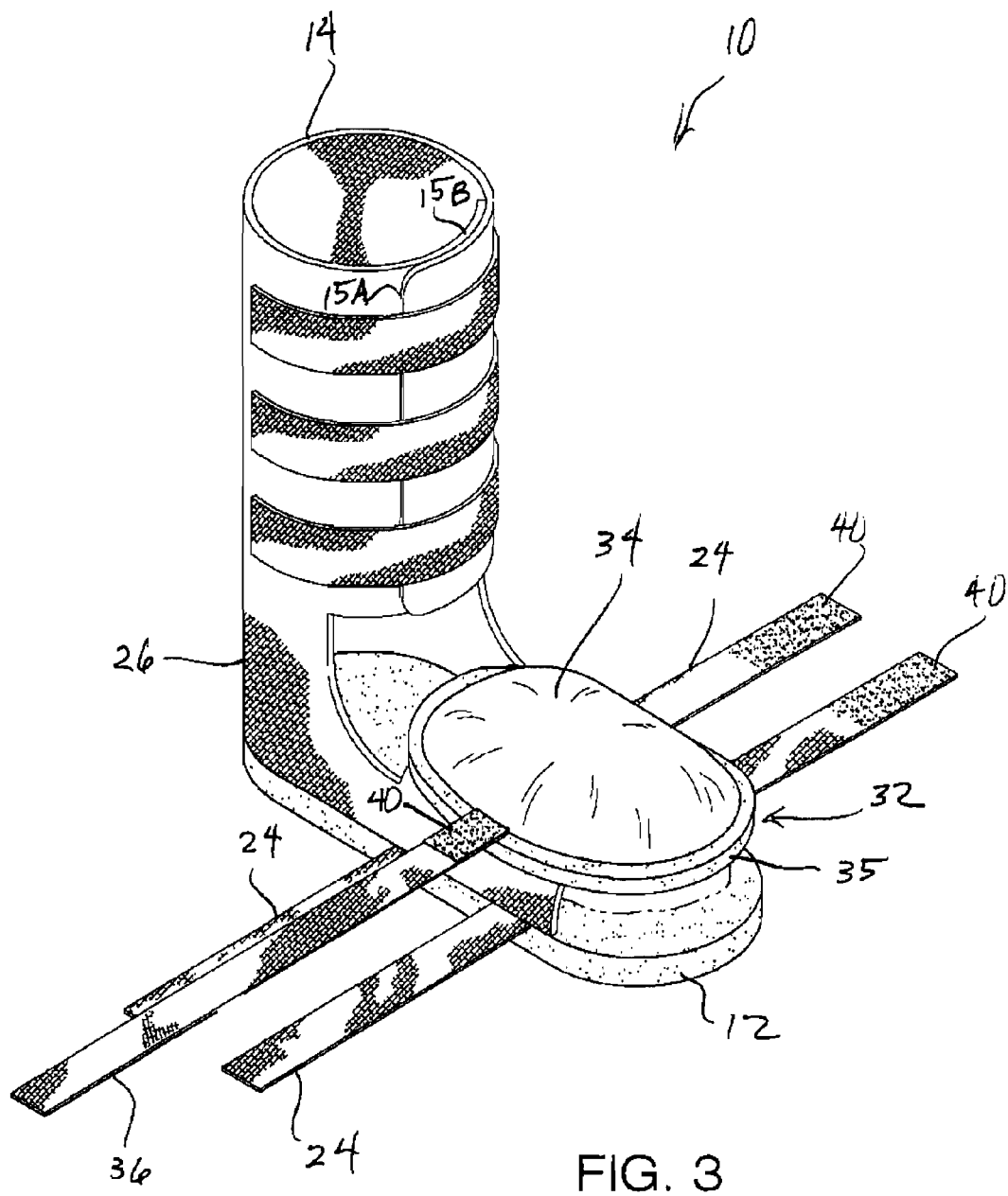
FIG. 3 is perspective view with foot straps and cover strap unfastened.
Figure 4:
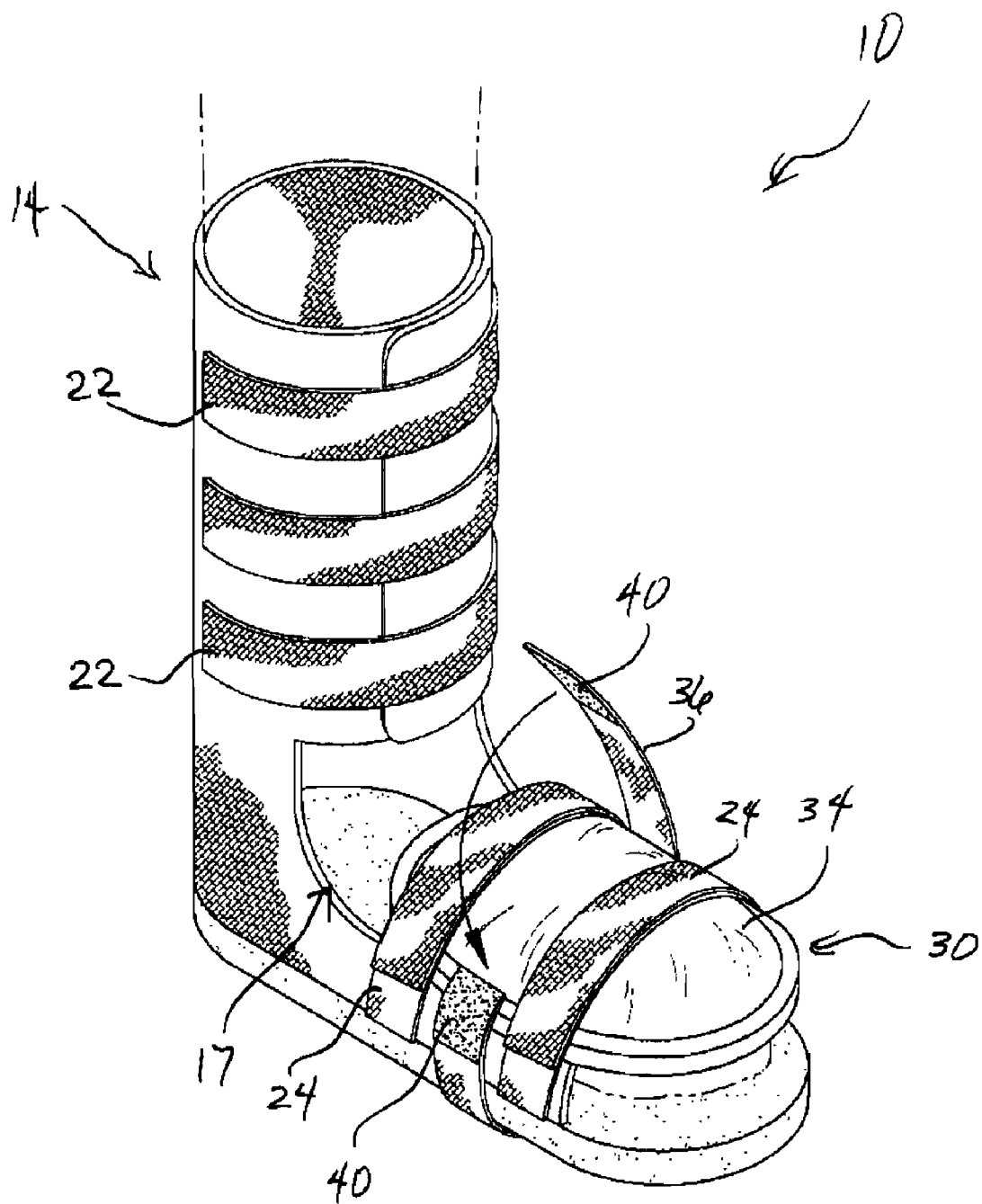
FIG. 4 is perspective view with cover strap unfastened.

With reference now to the drawings, and in particular FIGS. 1 through 5 thereof, the principles and concepts of the foot and ankle protective apparatus generally designated by the reference number 10 will be described.

Referring to FIGS. 1, 2, 3, and 4, the removable, adjustably fitted foot and ankle protective apparatus 10 is for use in walking. The apparatus 10 comprises a flexible sole 12 in one embodiment, and an inflexible sole 12 in another embodiment. One pliable foot surround 20 is affixed to each side of the sole 12. The foot surrounds 20 overlap over a user's foot 50. More than one spaced apart foot strap 24 is disposed on each side of the sole 12. Hook and loop 40 is disposed on each foot strap 24 such that the each corresponding foot strap 24 pair fastens to itself over a user's foot 50. The overlapping foot surrounds 20 provide for adjustable fit of the apparatus 10 to a given foot 50. The adjustable fit of the apparatus 10 provides for fitting different individual users. The apparatus 10 adjustable fit also provides for fitting a given user in the event that the user chooses to wear the apparatus 10 over clothing. The apparatus 10 further provides for adjustability for a given user in the event of limb swelling or swelling reduction. The pliable heel wrap 26 surrounds a heel of the user. The heel wrap 26 is connected to each foot surround 20. The pliable leg surround 14 is affixed to the heel wrap 26. The ankle opening 17 is disposed between the foot surrounds 20 and the leg surround 14. The first leg surround overlap A 15 is disposed on one side of the leg surround 14. The second leg surround overlap B 16 is disposed on an opposite second side of the leg surround 14. A plurality of spaced apart hook and loop 40 equipped leg straps 22 is affixed to the first leg surround overlap A 15. Hook and loop 40 (not shown) is disposed on the outside of the second leg surround overlap B 16 for fastening to the hook and loop 40 equipped leg straps 22. The leg surround overlap A 15 and leg surround overlap B 16 therefore provide for adjustable fit of a variety of leg sizes of various users. The adjustable fit of the apparatus 10 further provides for adjustable fit to a given user. Such adjustable fit might be applicable when a user wishes to wear the apparatus 10 on the outside of clothing items. The adjustable fit of the apparatus 10 further provides for adjustments due to limb swelling or swelling reduction of a limb.

Figure 5:
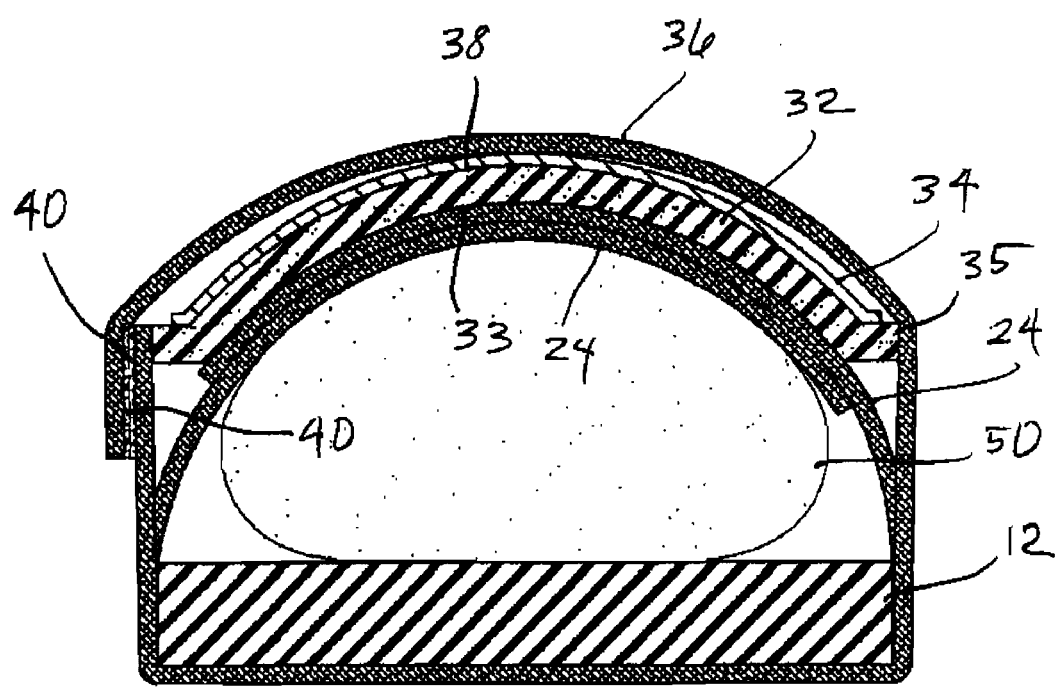
FIG. 5 is a partial cross sectional view of FIG. 1

Referring to FIG. 5, the foot cover 30 provides cushioned protection for a user's foot 50. The foot cover 30 comprises a cushion 32 of stadium plate shape. The lip 35 surrounds the cushion 32. The concave 33 is disposed on the inside of the cushion 32. The convex 38 is disposed on the outside of the cushion 32. The cover shell 34 is disposed on the convex 38 of the cushion 32. The cover strap 36 is attached to one side of the cover shell 34. Hook and loop 40 is disposed on the outside of the cover strap 36, proximal to the cover strap 36 attachment to the shell 34. Hook and loop 40 is disposed on the inside of and proximal to an end of the cover strap 36 opposite that of the cover strap 36 attachment to the shell 34.

With respect to the above description then, it is to be realized that the optimum dimensional relationships for the parts of the foot and ankle protective apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the foot and ankle protective apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the foot and ankle protective apparatus may be used.

Therefore, the foregoing is considered as illustrative only of the principles of the foot and ankle protective apparatus. Further, since numerous modifications and changes will readily occur to those skilled in the art, it is not desired to limit the foot and ankle protective apparatus to the exact construction and operation shown and described, and accordingly, all suitable modifications and equivalents may be resorted to, falling within the scope of the foot and ankle protective apparatus.

What is claimed is:

1. A removable, adjustably fitted foot and ankle protective apparatus for use in walking, the apparatus providing limited ankle flexion, the apparatus comprising:
   a flexible sole;
   a pliable foot surround affixed to an each side of the sole, the foot surrounds overlapping over a user's foot;
   more than one spaced apart foot strap on each side of the sole;
   hook and loop on each foot strap;
   a pliable heel wrap for surrounding a heel of the user, the heel wrap connected to each foot surround;
   a pliable leg surround affixed to the heel wrap;
   a pliable first leg surround overlap on a one side of the leg surround;
   a pliable second leg surround overlap on a second side of the leg surround;
   more than one spaced apart hook and loop equipped leg strap affixed to the first leg surround overlap;
   hook and loop on the second leg surround overlap for fastening to the hook and loop equipped leg straps;
   an ankle opening disposed between the foot surrounds and the leg surround;
   a removable foot cover; the foot cover comprising:
      a cushion of stadium plate shape;
      a lip surrounding the cushion;
      a concave on an inside of the cushion;
      a convex on an outside of the cushion;
      a cover shell on the convex;
      a cover strap attached to a one side of the shell;
      hook and loop on an outside of the cover strap, proximal to the cover strap-to-shell attachment;
      hook and loop on an inside of and proximal to an end of the cover strap opposite the strap-to-shell attachment.

\* \* \* \* \*